(12) United States Patent
Song et al.

(10) Patent No.: US 9,222,877 B2
(45) Date of Patent: Dec. 29, 2015

(54) FIBER BRAGG GRATING SYSTEMS AND METHODS FOR MOISTURE DETECTION

(71) Applicants: Gangbing Song, Pearland, TX (US); Siu Chun Michael Ho, Sugar Land, TX (US); Ren Liang, Dailan (CN)

(72) Inventors: Gangbing Song, Pearland, TX (US); Siu Chun Michael Ho, Sugar Land, TX (US); Ren Liang, Dailan (CN)

(73) Assignee: UNIVERSITY OF HOUSTON, Houston, TX (US)

( * ) Notice: Subject to any disclaimer, the term of this patent is extended or adjusted under 35 U.S.C. 154(b) by 219 days.

(21) Appl. No.: 14/054,156

(22) Filed: Oct. 15, 2013

(65) Prior Publication Data

US 2014/0102190 A1  Apr. 17, 2014

Related U.S. Application Data

(60) Provisional application No. 61/713,851, filed on Oct. 15, 2012.

(51) Int. Cl.
*G01N 21/17* (2006.01)
*G01M 3/04* (2006.01)

(52) U.S. Cl.
CPC ............... *G01N 21/17* (2013.01); *G01M 3/047* (2013.01); *Y10T 29/49117* (2015.01)

(58) Field of Classification Search
CPC ............... G01K 11/3206; G01L 1/246; G01N 2021/7723; G01N 21/7703; G01N 21/81; G02B 6/02; G02B 6/02095; G02B 6/02104
See application file for complete search history.

(56) References Cited

U.S. PATENT DOCUMENTS

| | | | |
|---|---|---|---|
| 3,562,731 A | 2/1971 | Hsu | |
| 5,120,131 A * | 6/1992 | Lukosz | G01N 21/7703 356/481 |
| 7,423,542 B1 | 9/2008 | Mitsis et al. | |
| 8,206,030 B1 | 6/2012 | Salour | |
| 2001/0030281 A1 * | 10/2001 | Schulz | G01M 3/165 250/227.21 |
| 2002/0041724 A1 * | 4/2002 | Ronnekleiv | A61B 5/01 385/12 |
| 2002/0130781 A1 | 9/2002 | Kroll et al. | |
| 2005/0105841 A1 * | 5/2005 | Luo | G01N 21/774 385/12 |
| 2006/0140559 A1 * | 6/2006 | Tsuda | G02B 6/02095 385/123 |
| 2006/0234621 A1 | 10/2006 | Desrochers et al. | |
| 2007/0065071 A1 * | 3/2007 | Slade | G01D 5/35303 385/12 |
| 2007/0107529 A1 * | 5/2007 | Maurin | G01B 11/165 73/800 |

(Continued)

FOREIGN PATENT DOCUMENTS

JP  08-184404 A  7/1996
WO  WO 2007/137429  12/2007

OTHER PUBLICATIONS

Laylor et al., "Fiber Optic Grating Moisture and Humidity Sensors", SPIE Proceedings 4694, International Society for Optical Engineering, 2002, pp. 210-217.*

(Continued)

*Primary Examiner* — David A Rogers
(74) *Attorney, Agent, or Firm* — Winstead PC (57) ABSTRACT

A fiber Bragg grating (FBG) sensor for detecting moisture may include a sensor housing, FBG cable, water-swellable bead(s), and retaining mechanism. The housing secures the FBG cable and water-swellable bead. The retaining mechanism, such as one or more wire(s), placed adjacent to the FBG cable may be utilized to minimize lateral displacement of the water-swellable bead(s). The water-swellable bead(s) may swell as they absorb water, thereby causing the FBG to be strained to allow the detection of liquid moisture.

26 Claims, 6 Drawing Sheets

(56) References Cited

U.S. PATENT DOCUMENTS

| | | | | |
|---|---|---|---|---|
| 2007/0116402 A1* | 5/2007 | Slade | ............... | G01N 21/7703 385/12 |
| 2009/0129721 A1* | 5/2009 | Chen | ............... | G01F 23/292 385/12 |
| 2009/0129722 A1* | 5/2009 | Hao | ............... | G01D 5/35383 385/13 |
| 2009/0269003 A1* | 10/2009 | Scully | ............... | G01N 21/7703 385/12 |
| 2010/0315630 A1* | 12/2010 | Ramos | ............... | G01D 5/3537 356/301 |
| 2011/0085759 A1* | 4/2011 | Lee | ............... | G01N 21/7703 385/12 |
| 2011/0200285 A1* | 8/2011 | Boersma | ............... | G01N 21/774 385/37 |
| 2012/0081696 A1* | 4/2012 | Boersma | ............... | G01D 5/268 356/73.1 |
| 2012/0177319 A1* | 7/2012 | Alemohammad | ............... | C03C 25/106 385/12 |

OTHER PUBLICATIONS

Kunzler et al., "Implementing Fiber Sensors to Monitor Humidity and Moisture", SPIE Proceedings 5384, Smart Structures and Materials 2004: Smart Sensor Technology and Measurement Systems, No. 54, Jul. 27, 2004.*

Correia et al., "Optical Fiber Relative Humidity Sensor Based on a FBG with a Di-Ureasil Coating", Sensors, No. 12, pp. 8847-8860, Jun. 27, 2012.*

Sethuraman, "Fiber-Bragg Grating (FBG) Based Chemical Sensor", Aug. 2008, pp. 4-5, 48 (online) retrieved on Feb. 16, 2014 from internet:<URL: https://digarchive.library.vcu.edu/bitstream/handle/10158/Gopa_Thesis_081108.pdf?sequence=5>.

Healy, William M., "Development of an Optical Fiber-Based Moisture Sensor for Building Envelopes", Building and Fire Research Laboratory, National Institute of Standard and Technology, Oct. 14, 2003, pp. 277-282.

Cong, Jun et al, "Fiber optic Bragg grating sensor based on hydrogels for measuring salinity", Sensors and Actuators B 87 (2002) pp. 487-490.

Yeo, T L et al, "Demonstration of a fibre-optic sensing technique for the measurement of moisture absorption in concrete", Smart Materials and Structures 15 (2006) pp. N40-N45.

Yeo, T L et al, "Monitoring Ingress of Moisture in Structural Concrete Using a Novel Optical-Based Sensor Approach", Journal of Physics: Conference Series 45 (2006) pp. 186-192.

Yeo, T.L. et al, "Fibre-optic sensor technologies for humidity and moisture measurement", ScienceDirect, Sensors and Actuators A 144 (2008) pp. 280-295.

PCT International Search Report and Written Opinion for PCT/US2013/ 065036 dated Mar. 13, 2014.

* cited by examiner

FIBER BRAGG GRATING SYSTEMS AND METHODS FOR MOISTURE DETECTION

RELATED APPLICATIONS

This application claims the benefit of U.S. Provisional Patent Application No. 61/713,851 to Song et al., filed on Oct. 15, 2012, which is incorporated herein by reference.

STATEMENT REGARDING SPONSORED RESEARCH

Not Applicable.

BACKGROUND OF INVENTION

Many sensor modalities have been developed to sense the presence of water in its different phases. A majority of such sensors were geared to measure humidity (water vapor) levels. Some examples of such sensors include mechanical hygrometers, animal hairs, psychrometers, etc. These sensors have had broad applications across agriculture, weather prediction, medicine, etc.

The introduction of electronics has allowed the miniaturization of humidity sensors and thus is more versatile in terms of deployment. Partly due to this increase in versatility, most of the currently used humidity sensors are electronically based. Electronic humidity sensors measure changes in electron transduction due to air humidity. Generally, these sensors can be categorized into capacitative, resistive, and gravimetric sensors.

Fiber Optic Water Sensors:

While the integration of electronic technologies allowed the miniaturization of humidity sensors, the development of fiber optics (FO) has opened new doors in regards to the precision, operation, low cost, and networking. FO-based sensors also have a unique resistance to water-related damage, in contrast to most commercially available electronic sensors, which may be vulnerable to circuit shorting due to contact with liquid moisture. A wide variety of fiber optical humidity sensors have already been produced, and can be divided broadly into spectroscopic, fluorescent, interferometric, and in-fiber grating sensors.

Spectroscopic FO sensors generally measure changes in the spectroscopic absorption of a humidity-sensitive chemical (e.g. cobalt chloride, Rhodamine B, crystal violet, etc.) arranged on a thin film. Spectroscopic FO sensors can have a wide humidity range and fast response times (e.g a range between 0 to 95% relative humidity and response within 2 minutes). Fluorescent based FO sensors measure the fluorescence of certain dyes due to photonic excitation. For example, a fiber optic fluorosensor in which the magnitude of the fluorescence emitted by a dye (e.g. perylenedibutryate) can be modulated by the level of humidity. Another mode of FO humidity sensing is to take advantage of materials that change refractive index based on changes in humidity. For example, plastic fiber optic coated may be coated with hydroxyethylcellulose, which swells and changes refractive index in the presence of humidity. Interferometric FO sensors measure the phase difference of two light waves from the same source is compared after reflection from a mirror. Some known FO humidity sensors use Mach-Zehnder, Sagnac, or Fabry-Perot interferometric configurations.

In-Fiber Grating Sensors:

In-fiber grating sensors include long period gratings (LPG) and fiber Bragg gratings (FBG). Both the LPG and the FBG possess a section of optical fiber core inscribed with periodic perturbations (grating) of refractive index. The difference between the LPG and FBG is the length of the grating (LPG: 100 µm to 1 mm, FBG: <1 µm). Changes in the cladding of an LPG sensor lead to changes in its transmission spectrum. This property has been used to develop several humidity and liquid-moisture LPG sensor. In order to measure parameters such as humidity, a mechanism must be used to translate humidity into one of the aforementioned physical parameters. Some have accomplished this by using humidity sensitive polymers. For example, a polymer may be coated over the FBG to measure the moisture content of soil. Swelling of the polymer due to absorption of moisture induced a longitudinal strain in the FBG, thus shifting the wavelength and signaling the level of humidity. The sensor had a linear response between 0 to 100% humidity with a response time limited by the swelling rate of the polymer. Alternatively, an FBG may be coated with polyimide, for which moisture-induced swelling produced tension of the FBG. Other FBG-based humidity sensors have a similar construction (polymer-induced straining of the FBG), with some modified for sensing salinity or other analytes. The aforementioned FBG sensors may utilize a thin coating of a water-swellable polymer to induce strain on the FBG, which require a complicated bonding process.

In contrast, an improved FBG sensor and method provides a separate, but adjacent, bead of superabsorbent material is used to absorb liquid moisture. Volumetric expansion of the bead translated to a bending strain of the FBG adjacent to the bead, thus shifting the reflected wavelength. Further, this sensor detects the presence liquid moisture instead of measuring humidity levels.

SUMMARY OF THE INVENTION

A Fiber Bragg Grating (FBG) sensor provides a moisture detection system. The FBG sensor may include a water-swellable bead, sensor housing, a FBG cable, and a retaining mechanism. In some embodiments, the bead may be sealed in a water permeable packet. The bead and FBG cable are placed in the housing, and the FBG cable is positioned to be in contact with the bead. The bead is a water-swellable so absorption of water causes the bead to exert strain on the FBG cable. In some embodiments, the retaining mechanism may utilize one or more superelastic wires. Superelastic wire(s) may be positioned to restrict lateral movement of the bead.

A method for manufacturing the sensor may include the steps of fabricating a sensor housing, wherein the sensor housing provides a top portion and a bottom portion, and the sensor housing provides at least one opening. A water swellable bead is placed in the bottom portion of the sensor housing, wherein the water swellable bead swells when absorbing a liquid. A fiber Bragg grating (FBG) cable is placed in the sensor housing, wherein the FBG cable is in contact with the water swellable bead. The water swellable bead may be secured in the sensor housing with a retaining mechanism, and the top portion may be secured to the bottom portion of the sensor housing.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

Fiber Bragg Grating (FBG) systems and methods for moisture detection are discussed herein. A FBG system may provide a sensor housing, FBG cable, water-swellable bead, and a retaining mechanism. The sensor housing secures the components of the FBG system. The sensor housing may be made from any suitable materials. The sensor housing provides one or more openings that allow moisture to enter the housing. The FBG cable is an optical fiber core inscribed with periodic perturbations of refractive index (gratings). A water-swellable bead is material that swells as it absorbs liquid. In a preferred embodiment, the water swellable bead is a super absorbent polymer (SAP). Further, the SAP may be contained in a water permeable packet. A SAP is a polymer that can absorb several hundred times its own mass. Nonlimiting examples of SAPs include sodium polyacrylate, cross-linked polyacrylates, starch-graft polymers, or the like. The water-swellable bead is positioned adjacent to the FBG cable so that the FBG contacts the water-swellable bead. Expansion of the water-swellable bead due to fluid absorption causes strain to the FBG cable. The strain created by the absorbed fluid causes the reflected wavelength of the FBG cable to shift, thereby allowing the sensor to detect moisture when such a shift is detected. The retaining mechanism restricts movement of the water-swellable bead in the sensor housing to prevent it from moving to an unsuitable position for detecting moisture. In some embodiments, the retaining mechanism may restrict longitudinal movement of the water-swellable bead. In some embodiments, the system may also provide a temperature sensor to compensation for temperature effects on the FBG cable.

The FBG systems and methods detect liquid moisture. The FBG systems and methods place the water-swellable bead adjacent to the FBG, thereby avoiding complicated bonding processes of other FBG humidity sensors. The FBG systems and methods provide a sensor that can be subjected to repeated loading cycles. The FBG systems and methods provide a sensor that can survive flooding conditions.

Figure 1A:
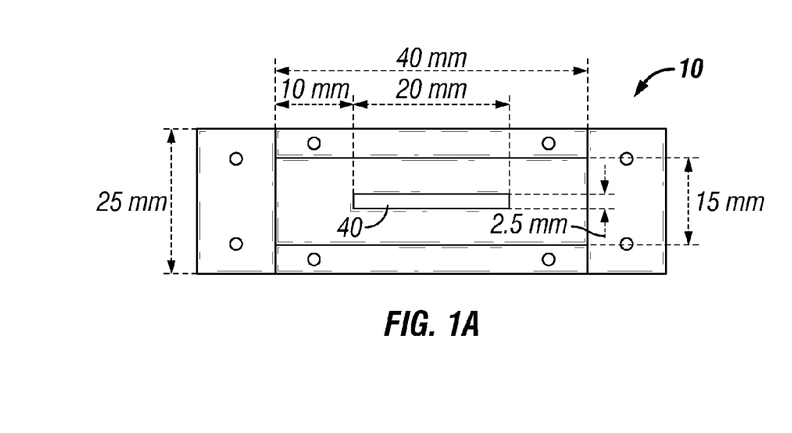
FIGS. 1A-1D are a top-down view of the housing without the middle cover, overall perspective of the water sensor housing, side view of the sensor housing, and axial view of the sensor housing respectively.
Figure 1B:
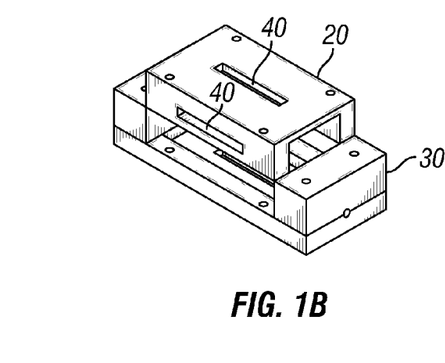
Figure 1C:
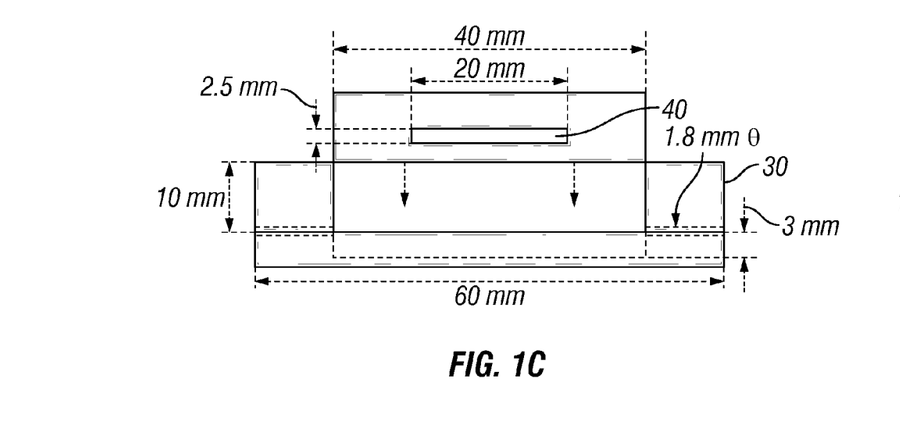
Figure 1D:
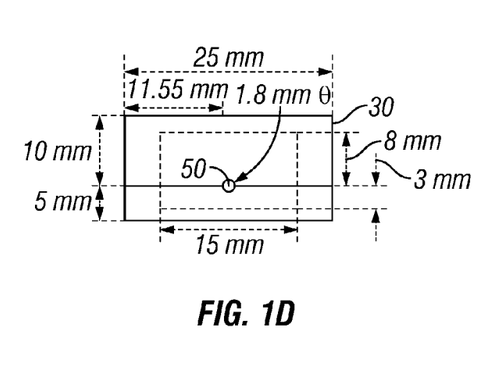

FIGS. 1A-1D are illustrative embodiments of a fiber Bragg grating (FBG) sensor housing. FIG. 1A is a top-down view of the housing without the middle cover; FIG. 1B is an overall perspective of the sensor housing; FIG. 1C is a side view of the sensor housing; and FIG. 1D is an axial view of the sensor housing. Sensor housing 10 may provide a top 20 and a base 30. Top 20 may provide one or more slots or openings 40. For example, slots 40 may be provided on a top and/or side surface of top 20. Slots 40 allow fluid to enter the sensing area. Fluid entering the slots or windows can reach past the package and be absorbed by the water-swellable bead. The volumetric expansion of the water-swellable bead due to water absorption directly tensions a FBG above the bead.

The sensor housing is designed to accommodate and protect both the FBG and the polymer bead(s) or sphere(s). Base 30 may provide conduits 50 on each side for the FBG to be positioned in the base. The conduits 50 may aligned the FBG through the longitudinal center of base 30. Parts of the FBG cable passing through the conduits 50 can be fastened to allow adequate strain transfer between the volumetric expansion of the polymer bead and the FBG. In some embodiments, the FBG fiber may be further protected by a thin furcation tube. Further, base 30 provides an open area below where the FBG cable is to be positioned for a water-swellable bead(s). The bead(s) may be any suitable water-swellable material, such as water-swellable polymer. In a non-limiting example, the water-swellable bead may be a super absorbent polymer (SAP), such as sodium polyacrylate, cross-linked polyacrylates, starch-graft polymers, or the like. In some embodiments, the polymer bead may be encased or surrounded within a silicon-sealed, thin-walled package made of water-permeable material in order to minimize the displacement of the polymer sphere and expand the area of contact with the FBG. The sensor housing may be made from any suitable material. In a non-limiting example, the sensor housing may be steel, plastic, or the like.

Figures 2, 3:
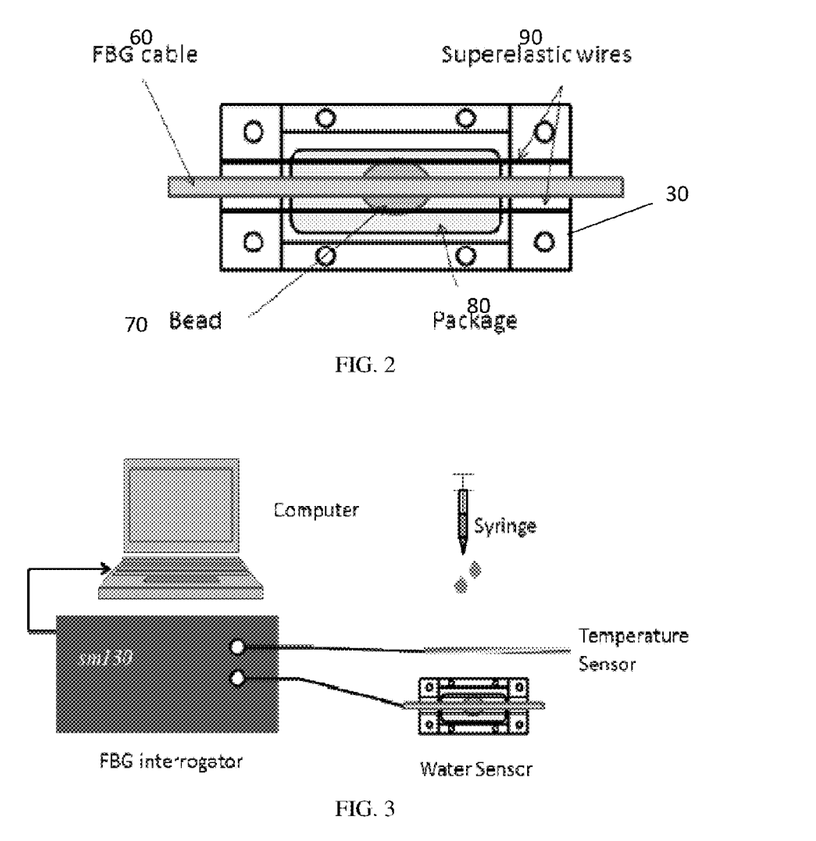
FIG. 2 is an illustrative embodiment of a sensor configuration.
FIG. 3 is an illustrative representation of an experimental set up.
Figure 4A:
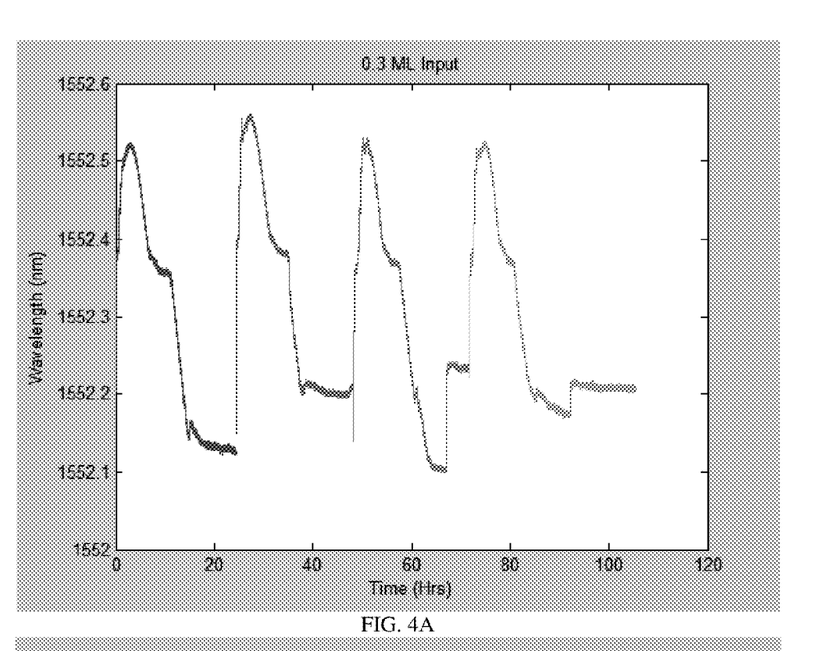
FIGS. 4A-4B show the results of sensor cycling at 0.3 mL and a corresponding zoom ins of the expansion profiles.
Figure 4B:
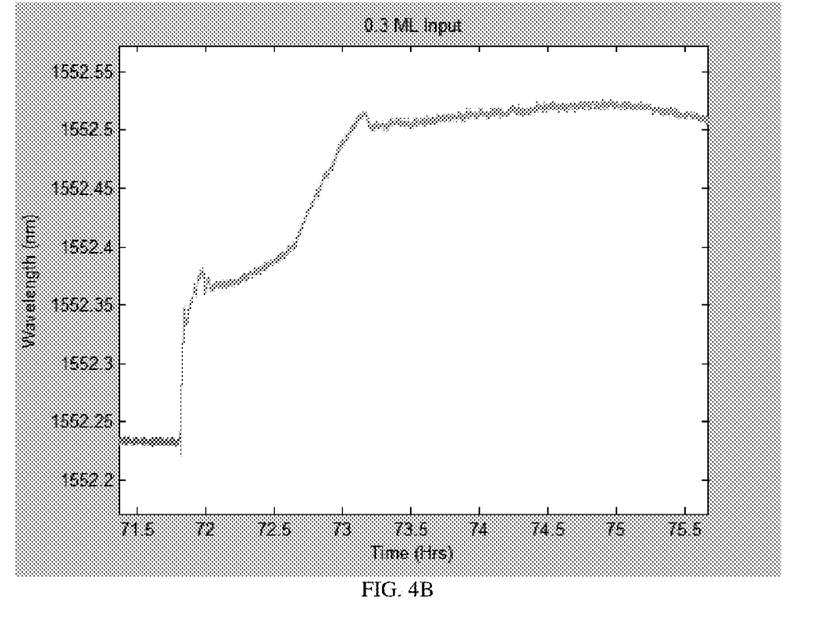
Figure 5A:
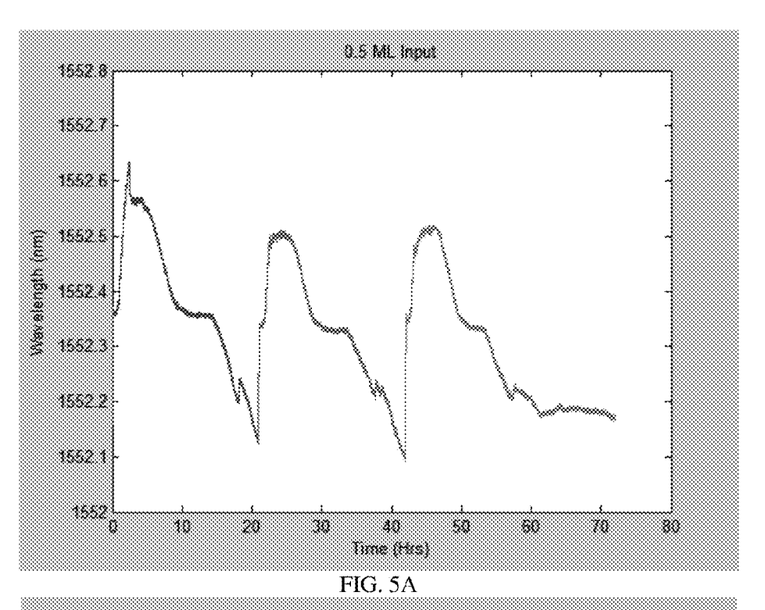
FIGS. 5A-5B show the results of sensor cycling at 0.5 mL and a corresponding zoom ins of the expansion profiles.
Figure 5B:
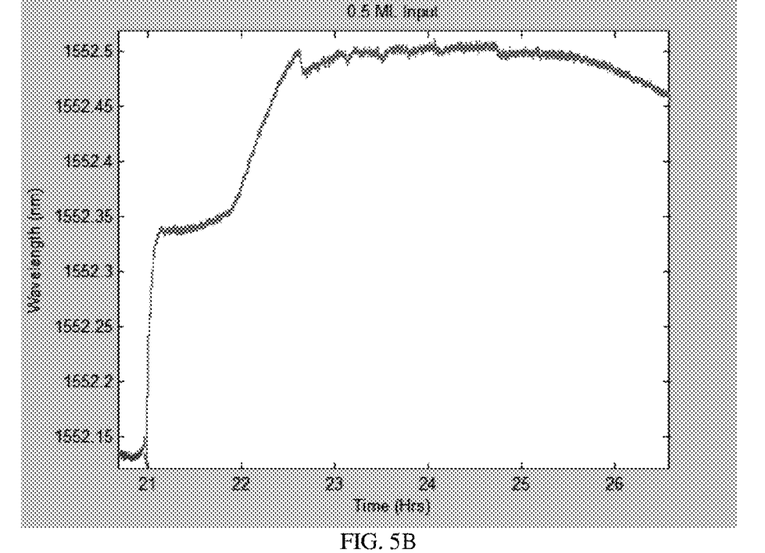
Figure 6A:
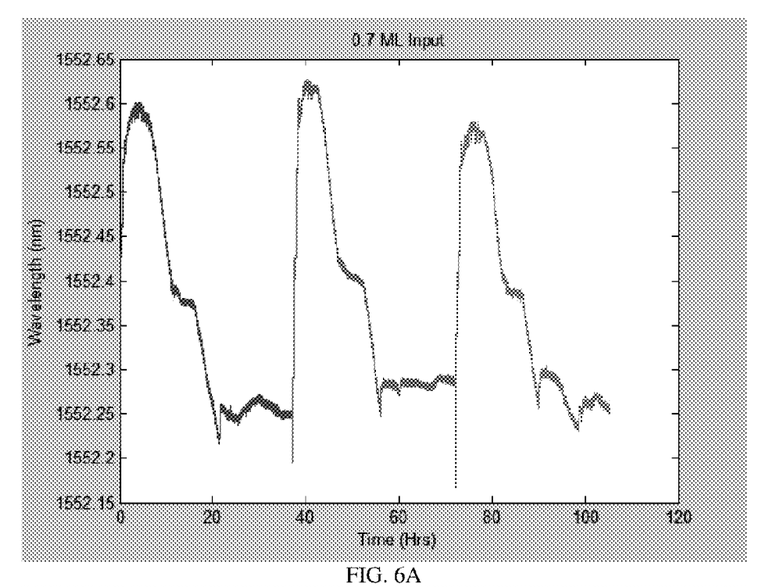
FIGS. 6A-6B show the results of sensor cycling at 0.7 mL and a corresponding zoom ins of the expansion profiles.
Figure 6B:
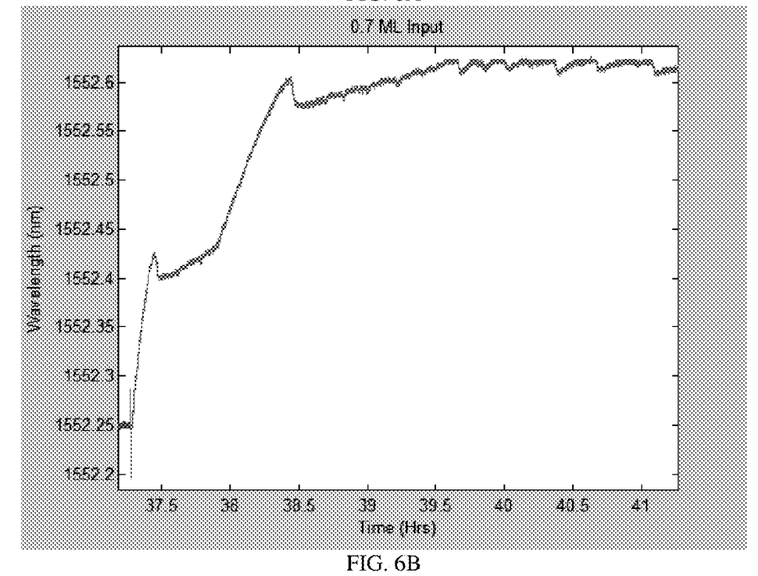

FIG. 2 is an illustrative embodiment of a sensor configuration. The sensor housing is shown without the top for purposes of clarity. Base 30 contains a FBG cable 60 and bead 70. Bead 70 is positioned in a package area 80 of the base 30. Water entering base 30, e.g. through slots in the top housing, may be absorbed by bead 70, thereby cause the bead to expand and cause strain on FBG cable 60. In some embodiments, a retaining mechanism 90, such as one or more wires, placed adjacent to the FBG cable 60 may be utilized to minimize lateral displacement of bead 70. In a non-limiting example, the wires may be superelastic wires, such as Nitinol wires. In order to minimize lateral displacement of bead 70 during swelling, two thin nitinol wires (0.1 mm diameter) run along the length of the housing offset (approximately 2 mm) from the central axis.

Bead(s) or Sphere(s):

The FBG sensor may utilize water-swellable beads. For example, a certain class of water-swellable polymers, called superabsorbent polymer (SAP) hydrogels, can absorb water several hundred times its own mass. SAPs can be seen as a network of crosslinked polymers containing ionic functional groups (e.g. carboxylate anions and sodium cations). The ionic groups produce a driving force that encourages water to be absorbed and retained within the polymer network. Together with elastic forces and polymer-solvent interactions, the ionic gradient comprises the osmotic pressure of the SAP. The SAP behaves so that the osmotic pressure is zero. In some embodiments, the SAP may be Sodium Polyacrylate $(C_3H_3NaO_2)_n$, which is a low cost SAP. This particular SAP relies on the —COONa functional groups to form an ionic potential that encourages the entry of water molecules into the polymer network. As more water enters the network, the functional groups become the less ionic —COOH group, thus slowing down the influx of water. The swelling characteristics of Sodium Polyacrylate with respect to different environmental variables (e.g. temperature, electrolyte concentration, pressure, etc) have been studied in detail. In other embodiments, the water-swellable bead may be cross-linked polyacrylates, starch-graft polymers, or the like. In a non-limiting example of a FBG sensor, one or more beads or spheres may be positioned along the FBG cable. The sensor has good repeatability and recovery properties. The sensor can be repeatedly exposed to loading cycles or repeatedly exposed to moisture and remain operable to detect moisture after a recovery time. In some embodiments, the response time of the sensor is 10 minutes or less. In some embodiments, the recovery time 15 hrs or less. Further, the sensor can be exposed to flooding conditions and will remain operable afterwards.

Manufacturing:

The sensor may be manufactured by placing the water-swellable bead into a water-permeable packet that is flexible to allow the expansion of the water-swellable bead. As discussed previously, the polymer may be a water-swellable polymer. In some embodiments, the water-swellable polymer is a super absorbent polymer (SAP). The polymer may be sealed within a packet. The packet is water permeable and will maintain sufficient elasticity when wet. The packet may aid the bead in transferring strain to the FBG cable. In non-limiting examples, the packet material may be a paper filter material, such as a lab grade filter paper, coffee filter, milk filter, hemp filter, tea bag paper, or the like. The pores of the packet material should not be large enough for the polymer material to expand through. Since the diffusion rate affects the response time of the sensor, the packet material can be selected in accordance with the level of responsiveness desired for the sensor. The polymer bead is placed in the packet, and the packet is sealed with a water resistant adhesive or the like. For example, the packet may be sealed by silicone gel sealant. The packet is placed underneath or adjacent to the FBG cable, and thus the expansion of the filled packet causes a strain in the FBG cable. In some embodiments, the sensor includes the installation of a retaining mechanism to secure the water-swellable bead in a desired position. For example, the retaining mechanism may be superelastic wire(s), such as shape memory alloy (SMA) wires, lying across the packet. The wires may help the packet return to a flattened shape once the polymer bead is dried up.

Additionally, if the water sensor is still accessible after it is deployed in the field, the user can interchange the old packet with a new one if needed (e.g. if a polymer sensitive to a certain chemical is desired or if some damage occurred in the original sensor). The sensor housing may be made of any suitable material for protecting the sensor from a deployment environment. For example, the nonlimiting embodiments discussed herein may utilize steel, other metals/alloys, plastic, or the like for the sensor housing. As such, the sensor housing may be manufacture by a machining process, casting, stamping, extrusion or any other suitable manufacturing process. In some embodiments, two or more FBG sensors may be multiplexed. Chaining multiple FBG sensors into one branch may allow multiple FBG sensors to be read by one channel. By chaining multiple FBGs together, one can form a large FBG sensor network while minimizing the amount of used channels in a data acquisition board.

An illustrative embodiment of a manufacturing process for the sensor can be summarized as follows:

1) Fabricate housing using adequately strong material.
2) Seal the polymer bead within the water permeable packet.
3) Place the polymer bead into the bottom half of the housing.
4) Place the FBG cable over the polymer bead. The housing may provide conduits to aid in properly aligning the FBG cable.
5) Place superelastic wire(s) across the polymer bead.
6) Place the top half of the housing over the whole assembly.
7) Secure the housing and FBG cable with fasteners or the like, such as screws or the like. To enhance sensitivity, the FBG may be prestrained. Prestraining may be done by stretching the FBG cable (e.g. to have +0.5 nm from center wavelength) and then carefully securing the FBG cable with fasteners or the like.
8) (optional) Multiplex with other FBG sensors.

Applications:

A FBG moisture sensor is suitable for use for a variety of purposes where moisture detection is important for structural health monitoring. Nonlimiting examples include structure monitoring (e.g. building, bridges, towers, tunnels, etc.), roadways, dams, seaside structures, nuclear facilities, etc. Concrete structures, which help form the basic infrastructure of modern society, must be designed to withstand a range of harsh environments. The longer the concrete structure has been in service, the higher the chance that the structure has sustained damage. Many times, damage is manifested in the form of cracks, and some make their way to the surface, where it can be seen by humans. However, damage propagating within the structure, such as near or at the reinforcing rebars, may not be as evident. Such internal damage may be attributed to the invasion of pure and/or ionized water into the structure, which may cause the corrosion of the reinforcing system of the concrete structure. Water may permeate through concrete in the form of humidity, or may even flow as moisture-liquid through concrete by traveling along conduits formed by cracks. The FBG systems and methods discussed herein may be utilized to detect the ingress of moisture and liquid water, and will be useful for a more complete structural health monitoring of any concrete construction.

Concrete structures rely much on the integrity of their supporting rebars to remain serviceable for their intended purposes. Moisture may enter the structure through cracks that may not be obvious to human observation. Unfortunately, rebars are vulnerable to corrosion due to the ingress of moisture from the environment, which often also carries a multitude of ionic particles that encourage corrosion. Thus, positioning the FBG systems discussed herein that are able to detect the presence of liquid moisture in such concrete structures would be beneficial.

Experimental Setup:

The following experimental examples are included to demonstrate particular aspects of the present disclosure. It should be appreciated by those of ordinary skill in the art that the methods described in the examples that follow merely represent illustrative embodiments of the disclosure. Those of ordinary skill in the art should, in light of the present disclosure, appreciate that many changes can be made in the specific embodiments described and still obtain a like or similar result without departing from the spirit and scope of the present disclosure.

Two tests were conducted on a sample FBG sensor as discussed herein: The first experiment tested the repeatability of the sensor to cyclic input of various volumes of water, and the second tested the sensor response to flooding conditions. The sensor showed a good repeatability, with fast response times (<10 minutes to reach a level guaranteeing the presence of water) and a recovery time of 11 to 15 hrs, depending on the input volume. The flooding test showed similar performance and viability of the sensor during flooding conditions.

Polymer Swelling Characterization:

The swelling limits of the polymer beads were tested. Ten measurements were made to random beads for dry and swollen measurements.

Sensor Cycling:

FIG. 3 is an illustrative representation of an experimental set up. Two FBGs (1560 nm and 1552 nm center wavelengths) were placed in two separate housings. Each FBG was pre-strained with a positive 0.5 nm shift (tension) before fixation at the conduits of the housing. A FBG based temperature sensor was placed in the nearby area to compensate for thermal effects. Each sensor was connected to an interrogator (Micron Optics sm130), which sent data via ethernet to a PC running ENLIGHT. Data was acquired in parallel for all three sensors at a rate of 1 Hz. To commence testing, a package containing one polymer bead was placed underneath the pretensioned FBG. A syringe was used to transfer drinking water from a local container to the sensors, including the temperature sensor. For the purposes of convenience, the middle cover section was not added, thus exposing the FBG and the package to the atmosphere. A small aluminum plate (10 mm×40 mm) was placed underneath the package to enhance water retention within the housing, and also promote contact between the package and the FBG. Table 1 summarizes the tests conducted with the sensors. The following tests were performed: 0.3 mL, 0.5 mL, and 0.7 mL. The same bead was used throughout the tests.

Flooding Simulation:

In the other test, a flooding scenario was simulated by immersing the sensors into a water bath to test the long term effects of exposure to the measurand. In anticipation of the swelling effects of the polymer, only half of a bead was used. The sensor was immersed for one day and allowed to dry for two days. This test performed twice.

Results

Polymer Swelling Characterization:

The average dry and swollen mass of the acquired sodium polyacrylate beads were found to be 0.019±0.003 g and 1.91±0.293 g, respectively. These values indicate the beads are able to carry an average of 1.89 mL of water (1 g/mL).

Sensor Cycling:

FIGS. 4A-6B show the results of sensor cycling at 0.3 mL, 0.5 mL, 0.7 mL, and corresponding zoom ins of their respective expansion profiles. It can be seen in FIGS. 4A-6B, the water sensor had good repeatability for each of cycling. Increase of the input volume lead to corresponding slight increase in the magnitude of the sensor response. Each cycle has a characteristic head-and-shoulders pattern in which the peak value of the output is preceded and proceeded by a mid-level plateau. Some discontinuity between cycles can be seen due to pausing and continuing data recording sessions.

TABLE 1

Summary of Cycle Tests

| Volume Input (mL) | Average Peak Amplitude from Rest (nm) | Average Time Start to Peak (Hrs) | Average Time Peak to Recovery (Hrs) |
|---|---|---|---|
| 0.3 | 0.3525 | 2.92 | 11.50 |
| 0.5 | 0.3953 | 3.88 | 13.22 |
| 0.7 | 0.4107 | 4.06 | 15.20 |

Figure 7A:
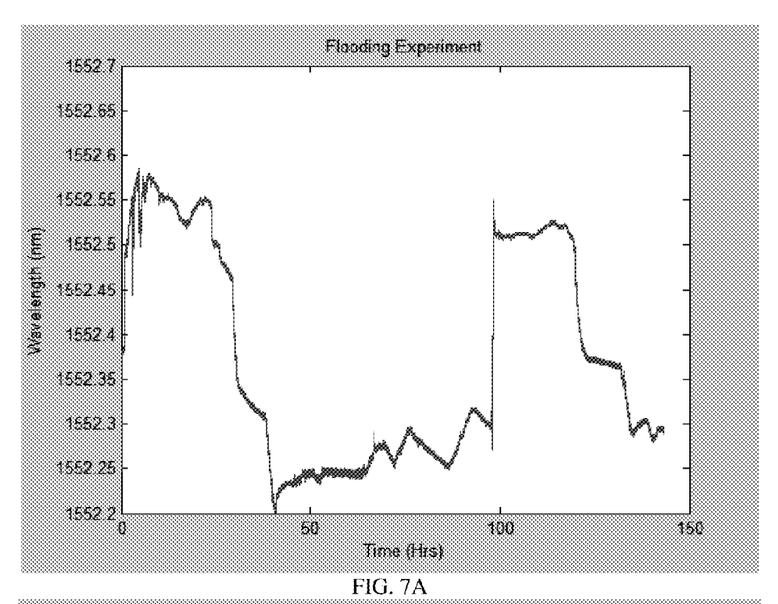
FIGS. 7A-7B show results of flood testing over 4 days and a zoom in of the first loading profile.
Figure 7B:
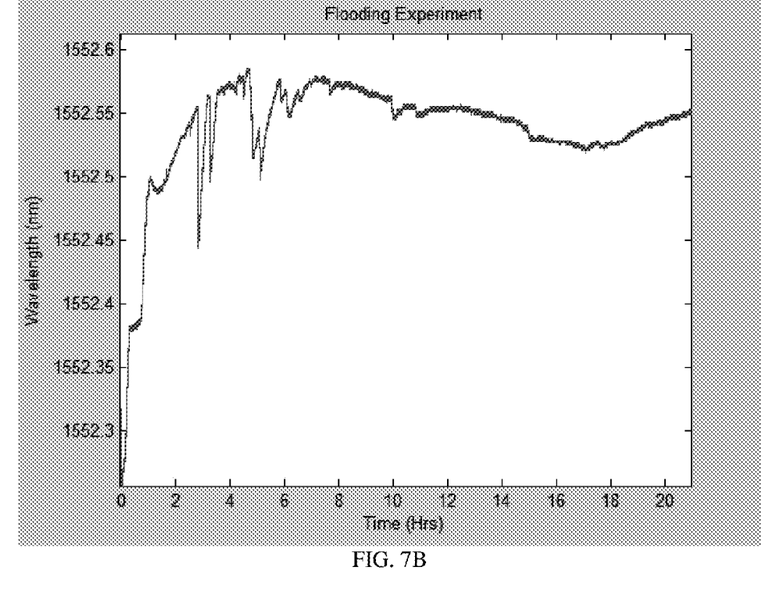

Flooding Test:

FIG. 7A-7B show the results of flood testing over 4 days and a zoom in of the first loading profile. The flooding test showed that the sensor was able to survive at least one day immersion into water. It was observed that the halved polymer bead expanded to fill the entire package and thus was permanently deformed after the first cycle. This change in geometry is further reflected by comparing the profile of the first (rough) and second (smooth) flooding cycle. Some oscillations in the signal were seen during the drying period and may be attributed to temperature effects not fully compensated by the temperature sensor.

Conclusions:

In order to better monitor the health of concrete structures, it is important to know if water has invaded and perhaps corroded the reinforcement system. A water sensor was designed to detect the presence of water (liquid moisture). With the installation of motion restriction measures for the sodium polyacrylate bead, the sensor had good repeatability through many loading cycles. The sensor has also shown to be viable for flooding conditions, and thus shows suitability for long term applications.

Implementations described herein are included to demonstrate particular aspects of the present disclosure. It should be appreciated by those of skill in the art that the implementations described herein merely represent exemplary implementation of the disclosure. Those of ordinary skill in the art should, in light of the present disclosure, appreciate that many changes can be made in the specific implementations described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure.

What is claimed is:

1. An apparatus for detecting moisture, the apparatus comprising:
   a moisture sensor that comprises
      a water swellable bead that swells when absorbing a liquid;
      a sensor housing for the water swellable bead, wherein the sensor housing provides a top portion and a bottom portion, and the sensor housing provides at least one opening;

a fiber Bragg grating (FBG) cable, wherein the FBG cable is positioned in the sensor housing in contact with the water swellable bead; and a retaining mechanism securing the water swellable bead in the sensor housing.

2. The apparatus of claim 1, wherein the water swellable bead is a superabsorbent polymer.

3. The apparatus of claim 2, wherein the superabsorbent polymer is sodium polyacrylate.

4. The apparatus of claim 1, wherein the water swellable bead is surrounded by a water permeable packet.

5. The apparatus of claim 1, wherein the retaining mechanism is superelastic wires, wherein the superelastic wires restrict lateral movement of the water swellable bead.

6. The apparatus of claim 5, wherein the superelastic wires are shape memory alloy wires.

7. The apparatus of claim 1, wherein the FBG cable is aligned through a longitudinal center of the sensor housing.

8. The apparatus of claim 1, wherein the FBG cable is placed in a furcation tube.

9. The apparatus of claim 1, wherein the FBG cable is fastened to conduits of the sensor housing.

10. The apparatus of claim 1, further comprising a temperature sensor.

11. The apparatus of claim 1, wherein the moisture sensor is operable after exposure to repeated load cycling.

12. The apparatus of claim 1, wherein the moisture sensor is operable after exposure to flooding conditions.

13. The apparatus of claim 1, wherein the moisture sensor is multiplexed with one or more additional moisture sensors, and each of the additional moisture sensors comprise the same components as the moisture sensor of claim 1.

14. A method for forming a sensor for detecting moisture, the method comprising:

fabricating a sensor housing, wherein the sensor housing provides a top portion and a bottom portion, and the sensor housing provides at least one opening;

placing a water swellable bead in the bottom portion of the sensor housing, wherein the water swellable bead swells when absorbing a liquid;

placing a fiber Bragg grating (FBG) cable in the sensor housing, wherein the FBG cable is in contact with the water swellable bead;

securing the water swellable bead in the sensor housing with a retaining mechanism; and securing the top portion to the bottom portion of the sensor housing.

15. The method of claim 14, wherein the water swellable bead is a superabsorbent polymer.

16. The method of claim 15, wherein the superabsorbent polymer is sodium polyacrylate.

17. The method of claim 14, further comprising surrounding the bead with a water permeable packet.

18. The method of claim 14, wherein the retaining mechanism is superelastic wires, wherein the superelastic wires restrict lateral movement of the water swellable bead.

19. The method of claim 18, wherein the superelastic wires are shape memory alloy wires.

20. The method of claim 14, wherein the FBG cable is aligned through a longitudinal center of the sensor housing.

21. The method of claim 14, wherein the FBG cable is fastened to conduits of the sensor housing.

22. The method of claim 21, wherein the FBG cable is prestrained when fastened to the sensor housing.

23. The method of claim 14, further comprising placing a temperature sensor in the sensor housing.

24. The method of claim 14, wherein the sensor is operable after exposure to repeated load cycling.

25. The method of claim 14, wherein the sensor is operable after exposure to flooding conditions.

26. The method of claim 14, further comprising:

repeating the steps recited in claim 14 to form one or more additional moisture sensors; and multiplexing the sensor with the one or more additional moisture sensors.

* * * * *